United States Patent [19]

Neuwirth et al.

[11] Patent Number: 5,492,529
[45] Date of Patent: Feb. 20, 1996

[54] TISSUE NECROSING APPARATUS AND METHOD FOR USING SAME INCLUDING TREATMENT OF BENIGN PROSTRATE HYPERTROPHY

[75] Inventors: Robert S. Neuwirth, Englewood, N.J.; Lee R. Bolduc, Raleigh, N.C.

[73] Assignee: Gynelab Products, Raleigh, N.C.

[21] Appl. No.: 809,653

[22] Filed: Dec. 18, 1991

[51] Int. Cl.⁶ ................................................. A61M 31/00
[52] U.S. Cl. .............................. 604/49; 604/114; 607/143
[58] Field of Search ............................... 604/49, 96, 101, 604/113–114; 606/27–28; 128/399–401; 607/96, 98, 99, 113, 115, 116, 143

[56] References Cited

U.S. PATENT DOCUMENTS

| | | | |
|---|---|---|---|
| 2,043,083 | 6/1936 | Wappler | 128/303.11 |
| 2,190,384 | 2/1940 | Newman | 128/400 |
| 4,160,455 | 7/1979 | Law | 128/400 |
| 4,638,806 | 6/1987 | Bartlett | 128/400 |
| 4,709,698 | 12/1987 | Johnstone et al. | 128/303.12 |
| 4,754,752 | 7/1988 | Ginsburg et al. | 128/303.12 |
| 4,762,128 | 8/1988 | Rosenbluth | 606/192 |
| 4,773,413 | 9/1988 | Hussein et al. | 606/28 X |
| 4,776,349 | 10/1988 | Nashef et al. | 128/786 |
| 4,799,479 | 1/1989 | Spears | 128/303.1 |
| 4,869,248 | 9/1989 | Narula | 606/45 |
| 4,932,956 | 6/1990 | Reddy et al. | 606/192 |
| 4,946,440 | 8/1990 | Hall | 604/95 |
| 4,978,346 | 12/1990 | Bentley | 606/27 |
| 4,979,948 | 12/1990 | Geddes et al. | 606/33 |
| 5,007,437 | 4/1991 | Sterzer | 428/786 |
| 5,037,395 | 8/1991 | Spencer | 604/113 |
| 5,041,124 | 8/1991 | Kensey | 606/170 |
| 5,045,056 | 9/1991 | Behl | 604/49 |
| 5,100,388 | 3/1992 | Behl et al. | 604/113 |
| 5,103,804 | 4/1992 | Abele et al. | 128/4 |
| 5,249,585 | 10/1993 | Turner et al. | 607/99 |

FOREIGN PATENT DOCUMENTS

| | | | |
|---|---|---|---|
| 459535 | 12/1991 | European Pat. Off. | 128/401 |
| 895046 | 12/1953 | Germany . | |
| WO91/03996 | 4/1991 | WIPO . | |
| 9200710 | 1/1992 | WIPO | 128/401 |

OTHER PUBLICATIONS

Outline of Presentation BBI–Innovative Surgical Devices and Technologies, Oct. 24, 1991, Biomedical Business International.

Transurethral Laser Treatment of Benign Prostatic Hyperplasia, D. L. McCulloch, MD, The Journal of Urology, vol. 146, 1126–1127, Oct., 1991.

Transurethral Ultrasound–guided Laser–Induced Prostatectomy (TULIP Procedure): A Canine Postate Feasibility Study, R. A. Roth, Md & H. Thomas Aretz, M.D., The Journal of Urology, vol. 146, 1128–1135, Oct., 1991.

Transcatheter Sclerosis of the Gallbladder in Rabbits A Preliminiary Study, G. I. Getrajdman, MD, et al., Investigative Radiology, vol. 20, 393–398, Jul., 1985.

Thermal Ablation of the Gallbladder, Carol C. Coleman, MD, et al.

*Primary Examiner*—Corrine M. Maglione
*Attorney, Agent, or Firm*—Kenyon & Kenyon

[57] ABSTRACT

A method and apparatus for necrosing tissue are disclosed. Also disclosed are a method and apparatus for treatment of urinary neck blockage and benign prostate hypertrophy. A catheter provided with a heating means and an inflatable balloon is inserted into the urethra so that the heating means is in proximity to the prostate gland and the inflatable bladder attached to the end of the catheter protrudes into the urinary bladder. The bladder is inflated in the urinary bladder to facilitate positioning of the heating means. The heating means is positioned and is then heated for a period of time sufficient to cause necrosis of the tissue lining of the prostate.

1 Claim, 4 Drawing Sheets

TISSUE NECROSING APPARATUS AND METHOD FOR USING SAME INCLUDING TREATMENT OF BENIGN PROSTRATE HYPERTROPHY

FIELD OF THE INVENTION

This invention relates to urological surgery and particularly to a tissue necrosing apparatus and method for performing prostate ablation. More specifically, an apparatus and method for treatment of benign prostate hypertrophy (BPH) is disclosed which effectively cauterizes and destroys the surface mucosa and more superficial tissue layers of the prostate gland at the urinary bladder neck.

BACKGROUND OF THE INVENTION

The following terms as used herein have the meaning given below:

The "mucosa" is a coating on the epithelial tissue of the prostate and the urinary bladder.

"Necrosis" means the death of cells in tissue.

"Superficial layers" means the outer layers of tissue, e.g., a depth of about 5-6 mm.

"Benign prostate hypertrophy (BPH)" is non-cancerous overgrowth of the prostate causing obstruction to urine outflow from the urinary bladder.

The standard treatment of BPH is transurethral resection of the prostate. Such procedures visualize the urinary bladder neck and the bulge of the hypertrophied prostate and remove part of the prostate by cutting and coagulative electrosurgery applied through a resectoscope. This treatment has significant disadvantages including exposure to electrosurgical burn, infusion of liquid distention media into the patient's vascular system that could cause congestive heart failure and serious electrolyte disturbances, hemorrhage from the prostate, and hospitalization.

Because of these disadvantages, improved technology for treatment of BPH has been sought. Alternative approaches have involved dilation of the urinary bladder neck, cryocoagulation of the prostate, and drug therapies to shrink the prostate or improve urinary bladder function. None of these methods has effectively replaced the transurethral prostatectomy with a urologic resectoscope. In contrast, the apparatus and method of the present invention effectively cauterizes and destroys the surface mucosa and superficial layers of the prostate gland at the urinary bladder neck, thus, reducing some and eliminating other disadvantages of resectoscopic removal of the prostate.

ADVANTAGES AND SUMMARY OF THE INVENTION

It is an advantage of this invention to provide a method and apparatus for performing partial prostatectomies which limits the risks of transurethral prostatectomy with the resectoscope while providing advantages of the transurethral approach to prostate destruction.

The present invention provides a balloon catheter device for necrosing tissue, comprising a) a tube having a proximal end and a distal end; b) a distendable bladder means extending from the distal end of the tube c) a passageway for inflation medium extending through the tube into the distendable bladder means; and d) a heating means for necrosing tissue disposed near the distal end of the tube so that inflation of the distendable bladder means facilitates positioning of the heating means.

The present invention also provides an apparatus for reducing bladder neck blockage caused by hypertrophied prostate comprising a) a tube having a proximal end and a distal end; b) a distendable bladder means having a proximal end and a distal end, the distendable bladder means adapted for insertion into the urinary bladder, the proximal end of the distendable bladder means attached the distal end of the tube; c) a heating means for heating the prostate to a temperature sufficient to effect tissue necrosis, the heating means attached to the distal end of the tube proximal to the distendable bladder means; d) inflating means connected to the proximal end of the tube for introducing an inflation medium into the distendable bladder means; and e) control means connected to the proximal end of the tube for regulating the temperature of the heating means.

The present invention also provides a method for reducing bladder neck blockage caused by a hypertrophied prostate comprising the steps of: a) providing a device for removing bladder neck blockage comprised of: a tube having a proximal end and a distal end; a heating means attached to the distal end of the tube for heating the prostate to a temperature sufficient to effect tissue necrosis; a distendable bladder means attached to the distal end of the tube, the distendable bladder means distal to the heating means and adapted for insertion into the urinary bladder; inflating means connected to the proximal end of the catheter tube for introducing an inflation medium into the distendable bladder means; and control means connected to the proximal end of the tube for regulating the temperature of the heating means; b) inserting the distendable bladder means into the urinary bladder; c) inflating the inserted distendable bladder means with an inflation medium to an appropriate volume sufficient to increase the diameter of the distendable bladder to a diameter larger than the diameter of the urethra; d) positioning the heating means so that the heating means is in proximity to the prostate; and e) heating the heating means to a temperature of about 150° to about 300° fahrenheit for a period of about 2 to about 10 minutes to effect necrosis of the tissue.

DESCRIPTION OF THE PREFERRED EMBODIMENTS

Figure 1:
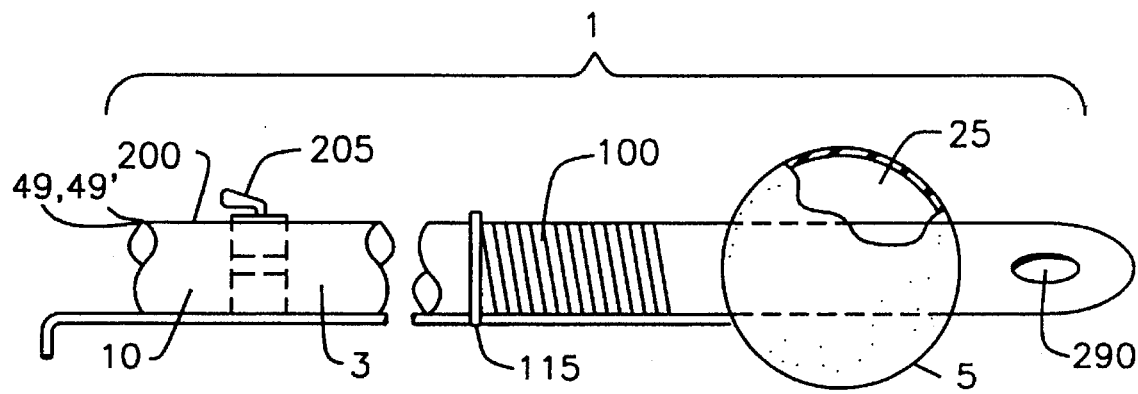
FIG. 1 illustrates a balloon catheter device constructed in accordance with the invention.

FIG. 1 shows a balloon catheter device 1 comprised of tubing 3 having a proximal and distal end, heating element 100, 100', or 101, inflation medium tubing 10, wires 49 and 49', and an inflated distendable bladder means 5. The distendable bladder means 5 is located on the distal end of tubing 3. The heating element 100, 100' or 101 is located on tubing 3 proximal to distendable bladder means 5. The distal end of heating means 100, 100' or 101 terminates about 2 mm proximal to the proximal end of inflatable bladder means 5. This results in a non-heated portion approximately 2 mm long on tubing 3. The non-heated portion of tubing 3 should be placed in proximity to the urinary bladder sphincter, thus, minimizing the potential for damage to the urinary bladder sphincter during treatment. The tubing 3 should possess the requisite rigidity and flexibility characteristics, well known to those skilled in the art, necessary for the tubing 3 to safely be inserted through an insertion path, e.g., the urethra 105 and into the urinary bladder 6. A modified Foley catheter (size 14 F) has been successfully utilized. The distendable bladder 5 when inflated with inflation medium 25 has a diameter larger than the diameter of the insertion path, e.g., the urethra 105. When the practitioner gently pulls the proximal end of tubing 3 away from the patient, the proximal portion of the distendable bladder 5 is forced against the posterior portion of the prostate 110. Thus, by pushing and pulling the proximal end of tubing 3, an operator can precisely position the heating element 100, 100' or 101, in this case with respect to the prostate 110. A thin non-stick coating 200 may be applied to the external surface of the balloon catheter device 1 to facilitate insertion and removal and to prevent adhesion of tissue to the device 1 after treatment. Precise positioning may be facilitated by positioning protrusion 115 located on the tubing 3 to indicate the position of the heating element 100, 100', or 101. Proper positioning of the heating element 100, 100' or 101 can be assured by inserting a finger into the rectum and palpating the positioning protrusion 115 at the prostatic apex near the ventral wall of the rectum. The positioning protrusion 115 may be positioned with respect to the inflatable bladder means 5 and heating means 100, 100', and 101 as specific applications dictate. A distance of about 2 cm from the proximal end of the inflatable bladder means 5 has proven satisfactory in many applications. The positioning protrusion 115 may be constructed of, or impregnated with, a radiographically visible material. The tubing 3 may be left in place for several days after surgery to provide a conduit for urine flow during the post-operative healing period. Urine enters the tubing 3 through opening 290. A valve 205 may be provided at the proximal end of tubing 3 to control post-operative urine flow.

Figure 2:
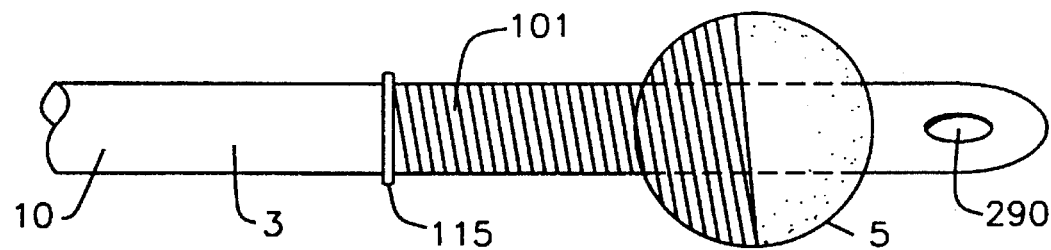
FIG. 2 illustrates a balloon catheter device constructed in accordance with another embodiment of the invention wherein the heating element extends beyond the distal end of the catheter and covers the proximal surface of the distendable bladder.

FIG. 2 illustrates an alternative embodiment having a heating element 101 that extends to and covers the external proximal surface of the distendable bladder 5. This embodiment facilitates necrosis of tissue on the posterior portion of the prostate 110. When the practitioner gently pulls the proximal end of tubing 3 away from the patient, the proximal portion of the distendable bladder 5 covered with heating element 101 is forced against the posterior portion of the prostate 110.

Figure 3:
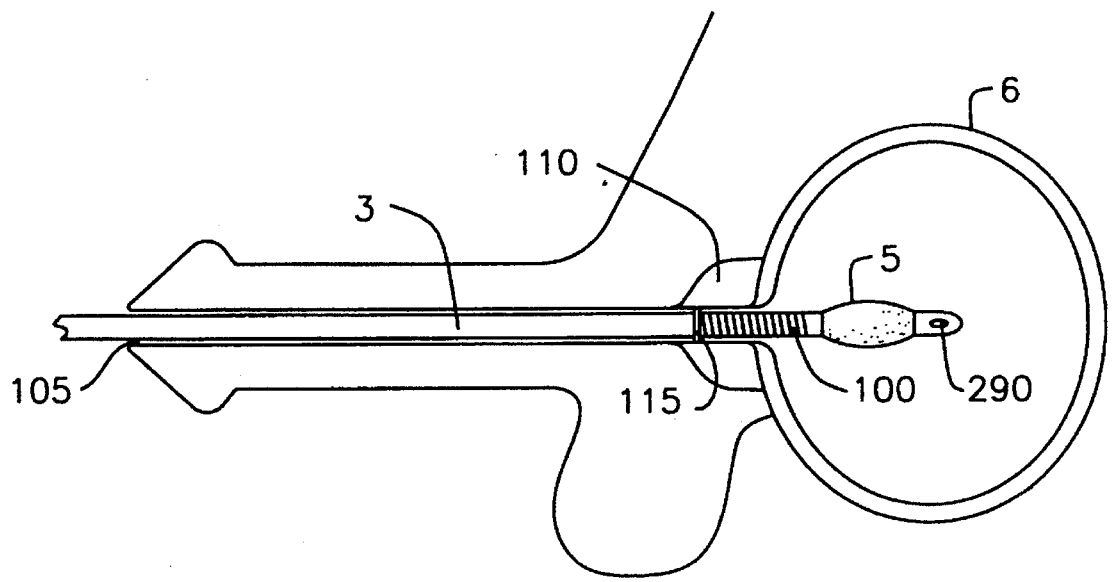
FIG. 3 illustrates an uninflated balloon catheter device of the invention inserted into the urinary bladder.

FIG. 3 is a sagittal view of a urethra 105, prostate gland 110, and urinary bladder 6 illustrating an uninflated balloon catheter device 1 of the invention inserted into the urethra 105. The uninflated distendable bladder 5 attached to the distal end of tubing 3 protrudes into the urinary bladder 6. The tubing 3 and the attached distendable bladder 5 must be sufficiently small, when the distendable bladder 5 is deflated, so that the device 1 can be conveniently and safely inserted into the urinary bladder 6 through the insertion path, e.g., the urethra 105.

Figure 4:
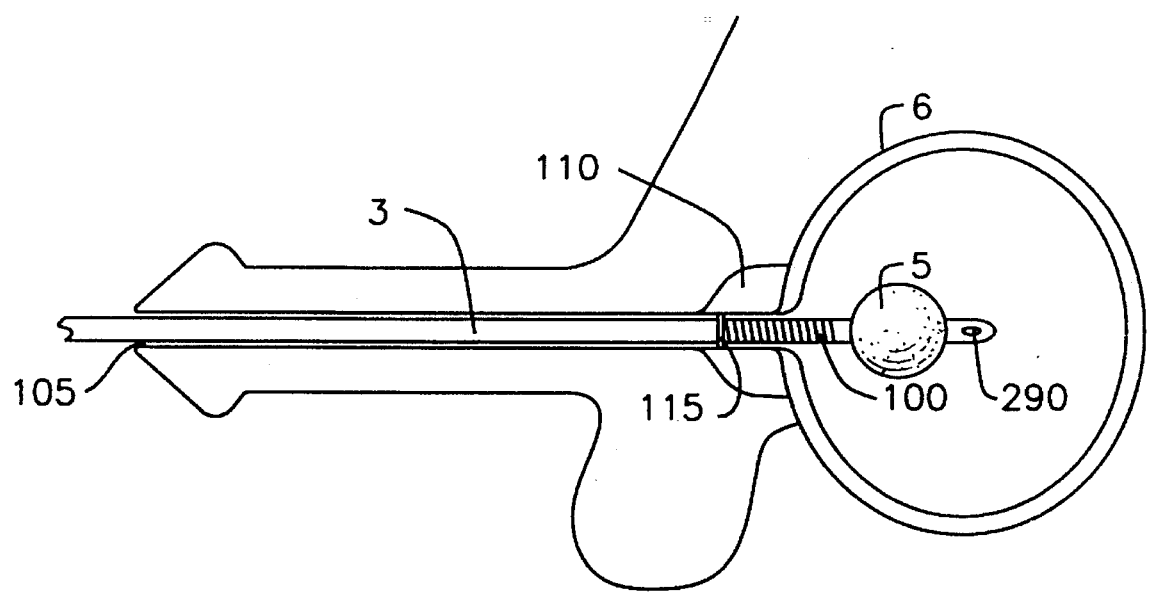
FIG. 4 illustrates a balloon catheter device of the invention inserted into and inflated within the urinary bladder.

FIG. 4 is a sagittal view of a urethra 105, prostate gland 110, and urinary bladder 6 illustrating insertion of the tubing 3 with attached heating element 100 and inflated distendable bladder 5 protruding into the urinary bladder 6.

After the distendable bladder 5 has been inserted into the urinary bladder 6, the distendable bladder 5 should be inflated to a pressure sufficient to enlarge the distendable bladder 5 so that it has a diameter greater than the diameter of the insertion path, e.g., the urethra 105. The pressure is preferably maintained at or about 20 to 40 mmHg, and more preferably about 30 mmHg, to minimize risk of rupture of the distendable bladder 5. Inflation medium 25 should be a sterile non-toxic fluid. A five percent dextrose in water solution has been found satisfactory.

Figure 5:
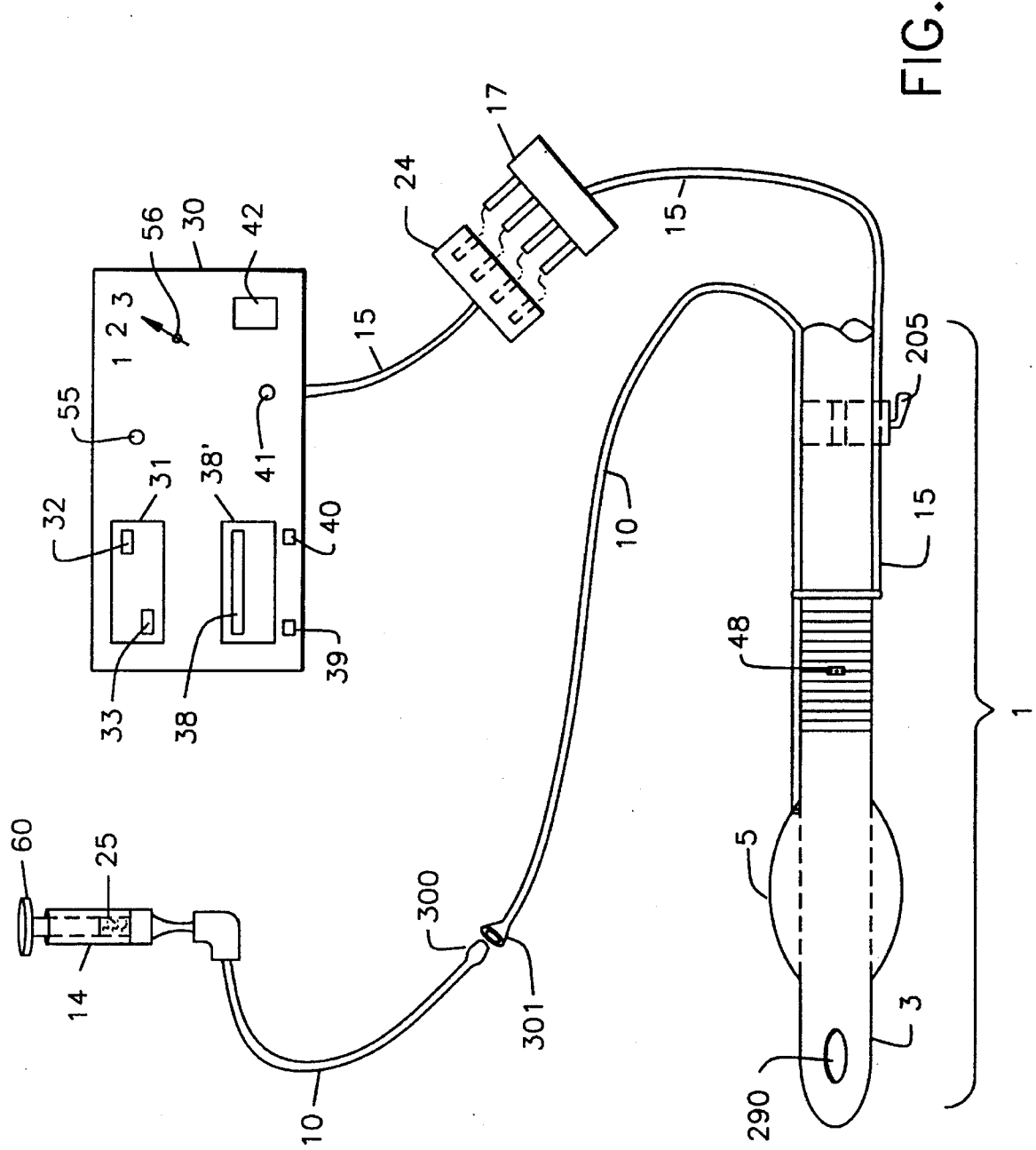
FIG. 5 is a view of a tissue necrosing system including a balloon catheter device; a system control unit; an inflation medium introduction means; a means for connecting and disconnecting the catheter constructed in accordance with the invention.

FIG. 5 illustrates the arrangement of a tissue necrosing system including control unit 30 and catheter device 1, comprising distendable bladder 5, tubing 3 and inflation medium tubing 10, and the interconnection of those elements. A fluid system comprises that portion of the invention through which the inflation medium 25 travels, including a hypodermic barrel 14 or other inflation medium source (not shown), inflation medium tubing 10, tubing 3, and distendable bladder 5. The operator of the system controls the amount of inflation medium 25 in the fluid system and inflation and deflation of the distendable bladder 5 by adding or removing inflation medium 25 via manipulation of the hypodermic plunger 60 in hypodermic barrel 14. When inflation medium 25 is introduced into inflation medium tubing 10 it flows into distendable bladder 5, forcing distendable bladder 5 to expand.

Figure 7:
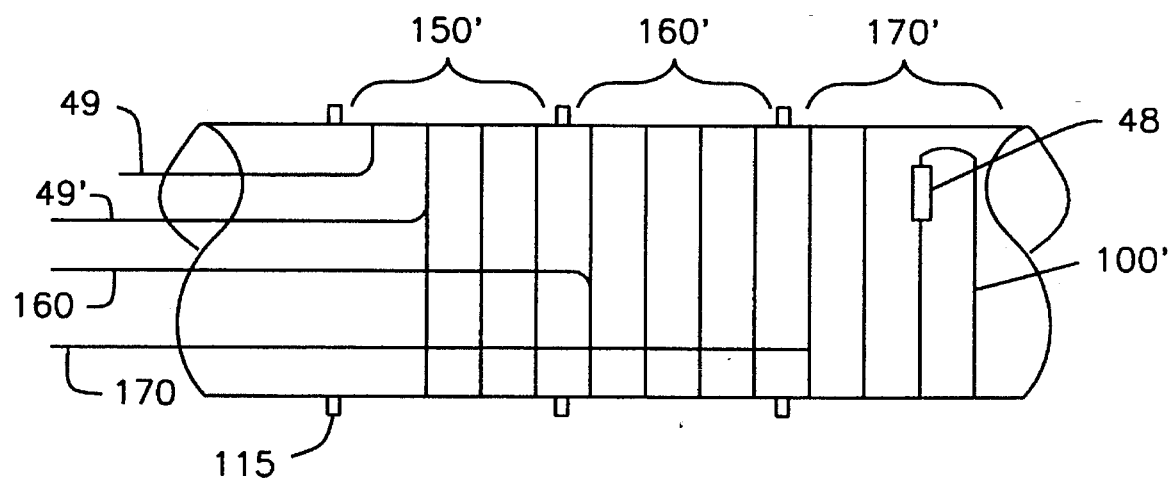
FIG. 7 illustrates a balloon catheter device constructed in accordance with the invention wherein portions of the heating means may be selectively heated.

Control unit 30 is connected to catheter device 1 via electrical sheath 15 which houses wires, e g , 49, 49', 160 and 170, which transmit electrical current to heating means 100, 100', and 101. Control unit 30 consists of heating element temperature control 31, time control 38' and a power source (not shown). The control unit 30 includes a power switch 42 and fuse 41. Heating element temperature is regulated by heating element temperature control 31 and is set by temperature set/reset button 33. The temperature of the heating element is shown at temperature display 32. A heating element indicator 55 is also provided to indicate when power is being provided to the heating element 100, 100', or 101 located on the tubing 3. In the embodiment utilizing heating element 100', heating coil length selector 56 may be used to selectively heat portions of heating element 100', e.g., 150', 160' and 170' by selectively passing current through wires that will selectively heat portions of heating means 100', e.g., 49', 160, or 170, as shown in FIG. 7.

Time for the procedure is shown at time display 38 which displays both lapsed time and time remaining for the procedure. Total time for the procedure may be easily set in minutes, seconds, and tenths of seconds using time set button 39 and may be cleared or reset using time clear/reset button 40.

The catheter device 1 is designed to be easy to replace or remove. Electrical sheath 15 is attached on one end to control unit 30 and on the other end to female electrical connector 24 which allows transmittal of power to the heating element 100, 100' or 101 via male electrical connector 17. Inflation medium tubing 10 is attached at one end to hypodermic barrell 14 and at the other end to male luer lock connector 300 which allows transmittal of inflation medium 25 to distendable bladder 5 via female luer lock connector 301.

Figure 6:
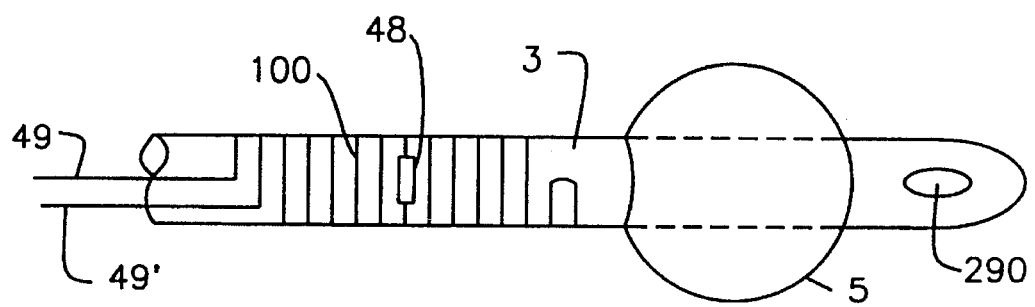
FIG. 6 is a side view of the heating element showing the heating element and thermocouple.

FIG. 6 is a side view of heating element 100, wherein wire leads 49 and 49' provide power from system control unit 30 to heating element 100 causing heating element 100 to heat the tissue in proximity to heating element 100. The temperature of heating element 100 is measured by thermocouple 48 and is displayed at temperature display 32. The heating element 100, 100' or 101 may be selected from a variety of successfully utilized heating elements well known to those skilled in the art. Wire having a diameter of about 0.0065 inches and a resistance of 13.5 ohms/ft. has proved satisfactory. Nicrome wire is especially advantageous. When wire is used as the heating element 100, 100' or 101 it should be wrapped around tube 3 approximately 20 turns/inch. The wire may be glued in place with, e.g., a silicone adhesive, and covered with a thin thermally transparent cover such as latex rubber.

FIG. 7 illustrates an alternative embodiment having means for selectively heating portions of heating element 100'. This embodiment allows for selected portions of the heating element 100' to be selectively heated, thus, providing greater precision in the application of heat to tissue. If the prostate 110 is relatively short along its axis surrounding the urethra 105, current should be passed through wire 49 and wire 170, with the result that only portion 170' of heating element 100' is heated. If the prostate 110 is of intermediate length along its axis surrounding the urethra 105, current should be directed through wire 49 and wire 160 which will heat portions 160' and 170' of the heating element 100'. If the prostate is relatively long along its axis surrounding the urethra 105, current should be passed through wire 49 and wire 49' which will heat portions 150', 160' and 170' of heating element 100'. A plurality of positioning protrusions 115 adjacent to portions 150' 160' and 170' facilitates positioning. It will be understood by those skilled in the art that the heating means 100' can be separated into as many portions as the specific application requires. An appropriate number of positioning protrusions may also be provided as required.

The necrosis procedure is preceded by placing the patient in the supine position. Cystoscopy will be performed to locate the urinary bladder sphincter, the prostrate obstructions and the urethral orifice. Rectal examination of the prostrate 110 and catheter device 1 locates positioning protrusion 115 to facilitate proper optimum positioning of the device. The rectal examination also provides guidance concerning the degree of blockage and the amount of prostate tissue to be treated, thus, also aiding the practitioner in determining the duration and temperature of treatment. The tube 3 provided with heating means 100, 100' and 101 and distendable balloon 5 is then inserted through the urethra 105 until the distendable balloon is within the urinary bladder 6.

After of the balloon catheter device 1 is inserted, the control unit 30 will be powered on in order to allow the practitioner to set the system constraints. The temperature of the heating element 100, 100' or 101 will be set at the temperature control panel and can be measured via thermocouple 48 located on heating element 100, 100' or 101.

The practitioner then inflates the distendable bladder 5 by injecting the inflation medium 25 into the system in order to reach the pressure wherein the distendable bladder 5 has a diameter larger than the diameter of the insertion path, e.g., the urethra 105.

The practitioner then heats the heating element 100, 100', or 101 to a pre-set temperature. The heating element 100, 100', or 101 is connected via electrical sheath 15 and control unit 30 to a 12 volt system which will heat the heating element 100, 100', or 101 to the level needed. When treating bladder neck blockage caused by a hypertrophied prostate, this temperature is about 150° to about 300° Fahrenheit. Once that temperature level is reached, the system timer is activated to time the procedure and provide automatic turn off of the heating element 100, 100', or 101 at the end of a pre-set period. A heating phase of from about 2 to about 10 minutes is preferred in order to completely necrose the superficial tissue layers.

Upon completion of the procedure, the inflation medium 25 is withdrawn from the system causing the distendable bladder 5 to deflate. Upon deflation of the distendable bladder 5, the balloon catheter device 1 may be safely withdrawn from the patient.

What is claimed is:

1. A method for reducing bladder neck blockage caused by a hypertrophied prostate comprising the steps of:

a) providing a device for removing bladder neck blockage comprising:

a tube having a proximal end and a distal end;

a wire coiled around said tube attached to said distal end of said tube for heating the prostate to a temperature sufficient to effect tissue necrosis;

a distendable bladder means attached to said distal end of said tube, said distendable bladder means distal to said heating means and adapted for insertion into the urinary bladder;

inflating means connected to said proximal end of said tube for introducing an inflation medium into said distendable bladder means; and control means connected to said proximal end of said tube for regulating the temperature of said wire;

b) inserting said distendable bladder means into the urinary bladder;

c) inflating said inserted distendable bladder means with an inflation medium to an appropriate volume sufficient to increase the diameter of said distendable bladder to a diameter larger than the diameter of the urethra;

d) positioning said wire so that said wire is in proximity to the prostate; and e) heating said wire to a temperature of about 150° to about 300° fahrenheit for a period of about 2 to 10 minutes to effect necrosis of the tissue.

* * * * *